US006255535B1

(12) United States Patent
Schulz et al.

(10) Patent No.: US 6,255,535 B1
(45) Date of Patent: Jul. 3, 2001

(54) FLUORINE CONTAINING ALLYLETHERS AND HIGHER HOMOLOGS

(75) Inventors: Jay F. Schulz, Eagan; George G. I. Moore, Afton, both of MN (US); Werner Schwertfeger, Bavaria (DE); Klaus Hintzer, Woodbury, MN (US); Zai-Ming Qiu, Woodbury, MN (US); Miguel A. Guerra, Woodbury, MN (US); Erik D. Hare, St. Paul, MN (US); Allan T. Worm, N. St. Paul, MN (US)

(73) Assignees: Dyneon LLC, Oakdale; 3M Innovative Properties Company, St. Paul, both of MN (US)

( * ) Notice: Subject to any disclaimer, the term of this patent is extended or adjusted under 35 U.S.C. 154(b) by 0 days.

(21) Appl. No.: 09/470,034

(22) Filed: Dec. 22, 1999

(51) Int. Cl.$^7$ .................................................. C07C 43/30
(52) U.S. Cl. ........................ 568/596; 568/615; 568/677; 568/685
(58) Field of Search .................................. 568/615, 616, 568/685, 596, 677

(56) References Cited

U.S. PATENT DOCUMENTS

| | | | |
|---|---|---|---|
| 2,713,593 | 7/1955 | Brice et al. | 260/535 |
| 4,273,728 | 6/1981 | Krespan | 260/465.6 |
| 4,379,901 | 4/1983 | Amimoto et al. | 526/247 |
| 4,433,180 | 2/1984 | von Werner | 568/684 |
| 5,326,917 | 7/1994 | Feiring et al. | 526/247 |
| 5,350,497 | 9/1994 | Hung et al. | 204/157.92 |
| 5,488,142 | 1/1996 | Fall et al. | 560/227 |
| 5,891,965 | 4/1999 | Worm et al. | 525/326.3 |

FOREIGN PATENT DOCUMENTS

| | | | |
|---|---|---|---|
| 0 290 848 | 11/1988 | (EP) | C07C/43/17 |
| 0 293 856 | 12/1988 | (EP) | C25B/3/08 |
| 0 334 796 | 3/1989 | (EP) . | |
| WO 98/50603 | 11/1998 | (WO) | C25B/3/08 |

OTHER PUBLICATIONS

J. Mohtasham: "Sulfur Trioxidation of Acyclic Fluoro–allyl Ethers: Synthesis of New Fluorinated Sultones and Their Derivatives", *Journal of Fluorine Chemistry*, vol. 43, 1989, pp. 349–369, XP–002147869 Lausanne CH p. 350.

"Modern Fluoropolymers", John Scheirs, Wiley Series in Polymer Science, 1997.

Emel 'yanov et al, Zh. Org. Khim, (1994) 30(8), pp. 1266–1270.

Adcock, James L. and William D. Evans, J. Org. Chem., vol. 49, p. 2719, (1984).

"Organic Reactions", vol. 1, p. 16 (1942).

*Primary Examiner*—Michael L. Shippen
(74) *Attorney, Agent, or Firm*—James V. Lilly

(57) ABSTRACT

The present invention describes a novel process for the preparation of perfluoro allyl ethers. The process involves providing a hydrogen-containing precursor comprising at least one 1,2-dichloro alkyl ether moiety, fluorinating the precursor to provide a perfluorinated intermediate, and dechlorinating the perfluorinated intermediate to the corresponding perfluorinated ether. A reaction product of a perfluorinated olefin and an allyl ether may also be used as a precursor. Such a reaction product is chlorinated before the fluorination step. Perfluoro vinyl or allyl ethers may be used in place of the perfluorinated olefin. Novel perfluoro alkoxy compounds are also described.

14 Claims, No Drawings

FLUORINE CONTAINING ALLYLETHERS AND HIGHER HOMOLOGS

FIELD

The present invention relates to perfluorinated allyl ethers and higher homologs and their preparation. These monomers are valuable comonomers for fluoroelastomers with enhanced low temperature properties.

BACKGROUND

The benefits of modifying fluoropolymers by allyl ethers are described in various review articles. See, for example, Modern Fluoropolymers, John Scheirs, Wiley Series in Polymer Science 1997 and in other literature (e.g. Emel 'yanov et al, Zh. Org. Khim (1994) 30(8) 1266–70; Krespan Carl G., DuPont de Nemours U.S. Pat. No. 4,273,728).

Perfluoro allyl ethers are known, e.g., Krespan Carl G.; DuPont de Nemours, U.S. Pat. No. 4,273,728 or Emel 'yanov et al, Zh. Org. Khim, (1994) 39(8) 1266–70 and Amimoto et al, Daikin U.S. Pat. No. 4,379,901. Long chain allyl ethers provide in fluoroelastomers excellent low temperature properties (see Worm et al, U.S. Pat. No. 5,891,965). A process to make perfluoro(alkyl vinyl ethers) by fluorination with elemental fluorine of selected novel partially fluorinated (di)chloroethyl ethers is described in U.S. Pat. No. 5,350,497 (Hung et al).

Alternative methods to prepare such materials from more commonly available starting materials are desirable. A particular need exists for a process to make linear perfluorinated allyl ethers.

SUMMARY

The present invention describes a process for the preparation of a perfluorinated ether of the formula $CF_2$=$CF(CF_2)_m$—O—$R_f$ wherein m=1–4 and $R_f$ is a linear or branched perfluorinated aliphatic group that may contain oxygen atoms thereby forming additional ether linkages. $R_f$ groups containing such oxygen atoms are referred to as perfluoroalkyleneoxy groups. $R_f$ preferably contains from 1–20, more preferably from 1 to 10, carbon atoms in the backbone. $R_f$ also contain additional terminal unsaturation sites.

Preferably, the perfluorinated ethers prepared according to the invention are perfluorinated allyl ethers of the formula $CF_2$=$CFCF_2$—O—$R_f$.

The perfluorinated allyl ethers may be either linear or branched. Preferably the perfluorinated allyl ethers are linear. As used herein, the term perfluorinated means that all of the carbon-bonded hydrogen atoms have been replaced with fluorine and any unsaturated carbon-carbon bonds have been saturated with fluorine.

One embodiment of the invention includes a process for the preparation of a perfluorinated ether of the formula $CF_2$=$CF(CF_2)_m$—O—$R_f$ wherein m has a value of from 1–4 and $R_f$ is a linear or branched perfluorinated aliphatic group that may contain oxygen atoms, the process comprising the steps of
(a) providing a hydrogen-containing precursor that may be partially fluorinated and which comprises at least one 1,2-dichloroalkyl ether moiety;

(b) fluorinating the hydrogen-containing precursor to provide a halogenated intermediate; and
(c) converting the halogenated intermediate to the perfluorinated ether.

A preferred embodiment of this process results when m=1. Another preferred embodiment results when $R_f$ is a linear perfluorinated aliphatic group that may contain oxygen atoms.

In another embodiment of the invention, a perfluorinated allyl ether is produced by a process comprising the steps of:
(a) providing a hydrogen-containing precursor by reacting a perfluorinated olefin, vinyl compound or an allyl compound with an allyl alcohol,
(b) chlorinating the hydrogen-containing precursor to provide a chlorinated intermediate,
(c) fluorinating the chlorinated intermediate to provide a perfluorinated product of step (b), and
(d) dechlorinating the product of step (c) to provide the perfluorinated allyl ether.

In a further embodiment of the invention, the allyl alcohol used in the reaction to produce the hydrogen-containing precursor described above is at least partially replaced by $HOCH_2CHClCH_2Cl$.

A still further embodiment of the invention provides perfluoro allyloxy compounds selected from the group consisting of $CF_3OC_3F_6OCF_2CF_2OCF_2CF$=$CF_2$, $CF_3OCF_2OCF_2CF_2OCF_2CF_2OCF_2CF$=$CF_2$, $C_2F_5OCF_2OCF_2CF_2OCF_2CF$=$CF_2$, $CF_3OCF_2CF_2OCF_2CF$=$CF_2$, $CF_3OCF_2OCF_2CF$=$CF_2$.

DETAILED DESCRIPTION

The perfluorinated allyl ethers prepared according to the present invention are useful in the preparation of fluoroelastomers, especially those that are used at low temperatures. Such elastomers are known. See, for example, U.S. Pat. No. 5,891,965 (Worm and Guerra).

The exact process used to make the perfluorinated ether is dependent upon the type of ether desired. However, there are certain process steps common to each of the embodiments of the invention. Fluorination of the precursors may be accomplished by either electrochemical fluorination (ECF) or direct fluorination (DF). ECF is described in U.S. Pat. No. 2,713,593 and in WO 98/50603. DF is described in U.S. Pat. No. 5,488,142.

We have found that direct fluorination of ethers of 2,3-dichloro-1-propanol unexpectedly gives good to excellent yields of the corresponding perfluorinated 1,2-dichloropropyl derivatives. Adcock (J Org Chem 49, 2719 (1984)) has shown that secondary alkyl chlorides give little or no corresponding perfluorinated secondary alkyl chlorides, either by apparent migration of the Cl atom to a primary position or by cleavage and loss of the Cl. Accordingly, direct fluorination of vicinal chlorides ($R'_hCHClCH_2Cl$) has not proven a useful method for the preparation of $R'_fCFClCF_2Cl$. Such perfluoro vicinal dichlorides are valuable because they are known to react with reducing agents such as metals to give $R'_fCF$=$CF_2$, useful as monomers and reagents.

It is thus surprising and useful that the class $R_hOCH_2CHClCH_2Cl$ does fluorinate to $R_fOCF_2CFClCF_2Cl$, which we have converted to $R_fOCF_2CF=CF_2$. Minor rearrangements to the perfluoro-1,3-dichloropropyl ether are seen for $R_h$=alkyl. This is less of a problem when $R_h$ is a partially fluorinated alkyl. There is no known theoretical basis for the stability of this class of ether-containing vicinal dichlorides in direct fluorination. In the above formula, $R_h$ can be alkyl or aryl and can be partially fluorinated. The corresponding $R_f$ will be perfluoroalkyl- or perfluorocyclohexyl. Both types of dichlorides can be converted to the corresponding perfluoroolefins. The advantage of this route lies in the moderate conditions and high overall yields in comparison to pyrolysis of perfluorocarboxylic acid salts as disclosed in U.S. Pat. No. 5,891,965.

Fluorination of the precursors can be done by electrochemical fluorination as previously described. However, direct fluorination is preferred due to fewer side products and improved yields. The solvents for fluorination are mostly perfluorinated compounds and/or fluorochloro compounds, e.g. perfluoromethylmorpholine, Freon 113, etc.

A perfluorinated allyl ether may be prepared by a process comprising the steps of:
(a) providing a hydrogen-containing precursor that may be partially fluorinated and which comprises at least one 1,2-dichloro alkyl ether moiety,
(b) fluorinating the chlorinated intermediate, and
(c) dechlorinating the fluorinated product of step (c) either in the presence of a metallic reducing agent or by an electrochemical means to provide the desired perfluoroallylether.

The 1,2-dichloro alkyl ether moiety may be a 1,2-dichloro propyl ether moiety, a 1,2-dichloro butyl ether moiety, a 1,2-dicliloro pentyl ether moiety, etc. depending upon the homolog desired. A 1,2-dichloro propyl ether moiety will yield an allyl ether in this context and is a preferred starting material. The hydrogen-containing precursor employed in this preparation can be partially fluorinated. The fluorination occurring in step (b) will replace all carbon-bonded hydrogen atoms with fluorine and also saturate with fluorine any unsaturated carbon-carbon bonds.

Preferred partially fluorinated precursors comprise the reaction product of (i) a perfluoro olefin or a perfluorovinyl or allyl ether and (ii) an allyl alcohol or higher homologs. More specifically, this embodiment of the invention may be exemplified by the following synthesis sequences.

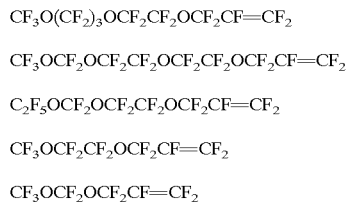

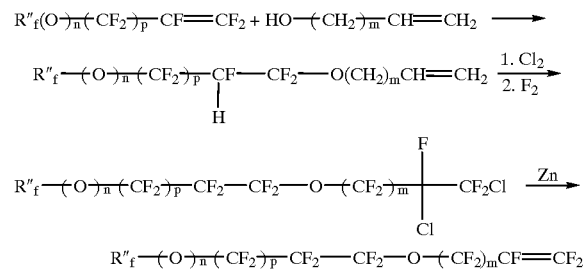

where m=1 to 4, p=0 to 4 and n=0 or 1. When p and n are 0, $R''_f$ is F or —$CF_3$. When n=1, $R''_f$ is $R_f$ as described above. A preferred embodiment results when m=1. This route opens new possibilities for the synthesis of perfluoroallyl ethers. The base catalyzed addition of perfluoroolefin to allyl alcohol is known and gives high yields of the partly fluorinated allyl ether. See U.S. Pat. No. 4,433,180 (von Werner).

When a hydrogen-containing precursor that comprises more than one 1,2-dichloro alkyl ether moiety is used, the corresponding allyl ether made from such a precursor may contain more than one unsaturation site. Possible examples include $CF_2=CFCF_2OR_fOCF_2CF=CF_2$ and $CF_2=CFOR_fOCF_2CF=CF_2$.

An additional starting material is also possible in this reaction sequence. This includes using $HOCH_2CHClCH_2Cl$ in place of at least a portion of the allyl alcohol.

Suitable olefins or reactants for the addition to allylalcohol include tetrafluoroethylene, hexafluoropropene, perfluoroalkyl vinyl ethers, such as perfluoromethylvinylether, perfluoropropylvinylether or perfluoroalkyl vinyl ethers as described in a copending application identified as U.S. Ser. No. 09/470,497, filed of even date herewith. Perfluoro alkyl allyl ethers are also useful. The preferred bases to catalyze the addition are alkali hydroxides KOH, NaOH, or NaOMe. Solvents for the reaction include N,N-dialkyl carboxylic acid amides or cyclic amides as described in U.S. Pat. No. 4,433,180 (von Werner).

Specific examples of perfluoro allyl ethers or allyloxy compounds that may be made by this route include:

$CF_3O(CF_2)_3OCF_2CF_2OCF_2CF=CF_2$ $CF_3OCF_2OCF_2CF_2OCF_2CF_2OCF_2CF=CF_2$ $C_2F_5OCF_2OCF_2CF_2OCF_2CF=CF_2$ $CF_3OCF_2CF_2OCF_2CF=CF_2$ $CF_3OCF_2OCF_2CF=CF_2$

The starting materials for the above allyl ethers may be made as described in the copending application listed above.

The addition of chlorine to the double bond of the partly fluorinated allylethers is generally done in solvent, e.g. Freon 113 or low boiling perfluorinated compounds.

The resulting perfluorodichloro compounds are dechlorinated by metals, such as, for example zinc, $Mg/HgCl_2$, $Mg_2/HgI_2$ or $LAH/TiCl_4$. Zn is the preferred agent, with the reaction done in dimethyl formamide (DMF) at higher temperatures (e.g., 100–150° C.). The alternative method is electrochemical dechlorination as described by Dapperheld in EP 293 856 and EP 334 796.

EXAMPLES

Example 1

Perfluoro methoxyethyl allyl ether

Methoxyethanol (100 g, 1.3 mol) was stirred with 51.3 g NaOH and 0.6 g Adogen 464 (methyltrialkyl ($C_8$–$C_{10}$) ammonium chloride, available from Aldrich Chemical Co.) and 155.1 g (1.3 mol) allyl bromide was slowly added with cooling initially and finally with external heating to 40° C. Filtration and distillation gave $CH_3OC_2H_2OCH_2CH=CH_2$ (bp 124–5° C.). A solution of 57.9 g (0.5 mol) of this allyl ether in 100 ml methylene chloride was treated with 39.8 g chlorine at about −40° C., purged with $N_2$, allowed to warm, and distilled to give 39.5 g $CH_3OC_2H_2OCH_2CHClCH_2Cl$, bp 110–115/4 mm. This chlorinated intermediate (523.7 g) was added at 11 to 11.5 ml/hr to 6885 g perfluoro-N-methylmorpholine (PMM) in a tubular reactor as described in U.S. Pat. No. 5,488,142 into which a gas stream comprised of 502 ml/min $F_2$ and 2005 ml/min $N_2$ was being introduced at a temperature of 25° C. Distillation yielded $CF_3OC_2F_2OCF_2CFClCF_2Cl$, bp 106–108° C. in 67% yield.

A stirred slurry of 41 g zinc dust, activated according to Organic Reactions vol. 1, p. 16 (1942), in 200 ml n-butanol was treated with 41.0 g of $CF_3OC_2F_2OCF_2CFClCF_2Cl$ and externally heated to 80° C. After 18 hr, the temperature was 70° C. with product refluxing. Direct distillation gave $CF_3OCF_2F_2OCF_2CF=CF_2$, bp 66–7° C.

1 were prepared in a manner similar to Example 5 except the HFP was replaced by the listed starting fluorinated olefin.

TABLE 1

| Ex. | Olefin | Product | Bp |
|---|---|---|---|
| 5 | $CF_3-CF=CF_2$ | $CF_3-CF_2-CF_2-O-CF_2-CF=CF_2$ | 60° C. |
| 6 | $CF_2=CF_2$ | $CF_3-CF_2-O-CF_2-CF=CF_2$ | 57° C. |
| 7 | $CF_3-O-CF=CF_2$ | $CF_3-O-CF_2-CF_2-O-CF_2-CF=CF_2$ | 67° C. |

Example 2
Perfluoro methoxyethyl allyl ether

A mixture of 16.0 g of $CF_3OC_2F_2OCF_2CFClCF_2Cl$ (from Example 1), 3.4 g ethanol, 50 g dioxane, and 9.8 g triphenylphosphine was stirred at reflux 16 hr. $^{19}F$ NMR showed 10% conversion and 9.8 g more triphenylphosphine was added. After 24 hr conversion to $CF_3OC_2F_4OCF_2CF=CF_2$ was 31%.

Example 3

In a procedure similar to Example 1, butyl allyl ether was chlorinated to $nC_4H_9OCH_2CHClCH_2Cl$, bp 94–100° C./12 mm, and this was fluorinated in $CF_2ClCFCl_2$ to $nC_4F_9OCF_2CFClCF_2Cl$ bp 123–30° C. $^{19}F$ NMR shows 12% to be the product of chlorine migration, $nC_4F_9OCFCl$ $CF_2CF_2Cl$. One could then dechlorinate the 1,2-dichloro compound described above to give the corresponding perfluorinated allyl ether.

Example 4
Perfluoro ethoxymethyl allyl ether

A mixture of 516 g (4.0 mol) 2,3-dichloro-1-propanol, 2.0 g toluenesulfonic acid hydrate, and 1500 ml (12.0 mol) diethoxymethane (DEM) was stirred at reflux while distilling out a mixture of ethanol and DEM. After 5 hr, 200ml had distilled and 250 ml fresh DEM was added. The reaction was shut off overnight and resumed the next day for 5 hr, reaching a final internal temperature of 99° C. Base wash and distillation yielded 688 g of $C_2H_5OCH_2OCH_2CHClCH_2Cl$, bp 60–70° C./0.3 mm. Of this amount, 210.7 g was fluorinated in PMM as in Example 1 and the product analyzed by $^{19}F$ NMR as containing $C_2F_5OCF_2OCF_2CFClCF_2Cl$ in 69% yield, accompanied by the 1,3-dichloride isomer in about 5% yield. Distillation gave the main cut bp 110° C., 96% pure by glc.

A mixture of 20.1 g $C_2F_5OCF_2OCF_2CFClCF_2Cl$, 20 g activated zinc, and 100 ml n-butanol was stirred at reflux 17 hr, final temperature 73° C. The product was directly distilled to 10.7 g, bp 60–90° C. Redistillation gave a main cut at 60–65° C., proven by $^{19}F$ NMR to be $C_2F_5OCF_2OCF_2CF=CF_2$ in 80% purity.

Example 5
Perfluoro propoxy allylether

Hexafluoropropene (HFP) was reacted at room temperature with a mixture of allylalcohol in dimethylformamide KOH-powder and a slight increase in pressure. The isolated allylether (bp 95° C.) was chlorinated with $Cl_2$ in Freon 113 at 30° C. to provide a chlorinated intermediate. Without isolation, the chlorinated intermediate was fluorinated by using a tubular reactor described in U.S. Pat. No. 5,488,142. After fluorination the solvent was distilled off and the remaining liquid was dropped in a stirred mixture of Zn in DMF at 150° C. The perfluoroallylether that resulted was condensed and rectified to obtain a higher purity. A boiling point (bp) of 60° C. was measured. The allylethers in Table

Example 8

In a procedure similar to Example 5, perfluoropropyl vinyl ether was reacted with allyl alcohol to produce $C_3F_7OCHFCF_2OCH_2CH=CH_2$. A solution of 756 g in 600 ml dichloromethane was treated with excess chlorine at –40° C. and the product distilled to a main cut of 940 g $C_3F_7OCHFCF_2OCH_2CHClCH_2Cl$ at 185–186° C. This was fluorinated as in Example 1 and the product $C_3F_7OCF_2CF_2OCF_2CFClCF_2Cl$ was confirmed in the crude mixture at 73% yield. Distillation gave a main cut at 144–149° C. One could then dechlorinate this as described above to give the corresponding perfluorinated allyl ether.

What is claimed is:

1. A process for the preparation of a perfluorinated ether of the formula

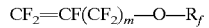

$$CF_2=CF(CF_2)_m-O-R_f$$

wherein m has a value of from 1–4 and $R_f$ is a linear or branched perfluorinated aliphatic group that may contain oxygen atoms, the process comprising the steps of (a) providing a hydrogen-containing precursor that comprises at least one 1,2-dichloro alkyl ether moiety;

(b) fluorinating the hydrogen-containing precursor to provide a halogenated intermediate; and (c) converting the halogenated intermediate to the perfluorinated ether.

2. A process according to claim 1 wherein the 1,2-dichloro alkyl ether moiety is a 1,2-dichloro propyl ether moiety.

3. A process according to claim 1 wherein m is 1.

4. A process according to claim 1 wherein $R_f$ is a linear perfluorinated aliphatic group that may contain oxygen atoms.

5. A process according to claim 1 wherein the hydrogen-containing precursor comprises more than one 1,2-dichloro alkyl ether moiety.

6. A process according to claim 1 wherein the hydrogen-containing precursor of step (a) is partially flurionated.

7. A process for the preparation of a perfluorinated allyl ether comprising the steps of:

(a) providing a hydrogen-containing precursor by reacting a perfluorinated olefin, a vinyl compound or an allyl compound with an allyl alcohol;

(b) chlorinating the hydrogen-containing precursor to provide a chlorinated intermediate;

(c) fluorinating the chlorinated intermediate to provide a perfluorinated product of step (b); and (d) dechlorinating the product of step (c) to provide a perfluorinated allyl ether.

8. A process according to claim 7 wherein dechlorination occurs either in the presence of a metallic reducing agent or is achieved by electrochemical means.

9. A process according to claim 8 wherein the metallic reducing agent is Zn.

10. A process according to claim 7 wherein the perfluorinated ether has the formula $CF_2=CF-CF_2-O-R_f$.

11. A perfluoro allyloxy compound having the formula $$CF_3O(CF_2)_3OCF_2CF_2OCF_2CF=CF_2.$$

12. A perfluoro allyloxy compound having the formula $$CF_3OCF_2OCF_2CF_2OCF_2CF_2OCF_2CF=CF_2.$$

13. A perfluoro allyloxy compound having the formula $$C_2F_5OCF_2OCF_2CF_2OCF_2CF=CF_2.$$

14. A perfluoro allyloxy compound having the formula $$CF_3OCF_2OCF_2CF=CF_2.$$

* * * * *